(12) United States Patent
Lewis et al.

(10) Patent No.: US 7,153,991 B2
(45) Date of Patent: Dec. 26, 2006

(54) ROCHOW-MÜLLER DIRECT SYNTHESIS USING NANOSIZED COPPER CATALYST PRECURSORS

(75) Inventors: Kenrick M. Lewis, Rego Park, NY (US); James S. Ritscher, Marietta, OH (US)

(73) Assignee: General Electric Company, Schenectady, NY (US)

(*) Notice: Subject to any disclaimer, the term of this patent is extended or adjusted under 35 U.S.C. 154(b) by 157 days.

(21) Appl. No.: 09/974,266

(22) Filed: Oct. 9, 2001

(65) Prior Publication Data
US 2003/0032829 A1    Feb. 13, 2003

Related U.S. Application Data

(60) Provisional application No. 60/250,915, filed on Dec. 1, 2000.

(51) Int. Cl.
*C07F 2/16* (2006.01)

(52) U.S. Cl. ......................... 556/472; 556/466

(58) Field of Classification Search ............... 556/466, 556/472
See application file for complete search history.

(56) References Cited

U.S. PATENT DOCUMENTS

| | | | |
|---|---|---|---|
| 2,380,995 A | | 8/1945 | Rochow et al. |
| 3,428,530 A | * | 2/1969 | Fauche et al. ............... 203/72 |
| 3,505,379 A | | 4/1970 | Bonitz et al. |
| 4,450,282 A | | 5/1984 | Ritzer et al. |
| 4,762,940 A | | 8/1988 | Halm et al. |
| 4,864,044 A | | 9/1989 | Lewis et al. |
| 4,946,980 A | | 8/1990 | Halm et al. |
| 5,759,230 A | | 6/1998 | Chow et al. |
| 5,880,307 A | * | 3/1999 | Daugherty et al. ......... 556/472 |
| 6,057,469 A | * | 5/2000 | Margaria et al. ............ 556/472 |
| 6,090,966 A | * | 7/2000 | Nakanishi et al. ......... 556/472 |
| 6,288,258 B1 | * | 9/2001 | Aramata et al. ............ 556/472 |
| 6,339,167 B1 | * | 1/2002 | Aramata et al. ............ 556/472 |
| 6,407,276 B1 | * | 6/2002 | Lewis et al. ............... 556/472 |
| 6,423,860 B1 | * | 7/2002 | Lewis et al. ............... 556/472 |
| 6,506,923 B1 | * | 1/2003 | Inukai et al. ............... 556/472 |
| 6,528,674 B1 | * | 3/2003 | Lewis et al. ............... 556/472 |

FOREIGN PATENT DOCUMENTS

| | | |
|---|---|---|
| DE | 5348 | 6/1942 |
| DE | 920 187 | 11/1954 |
| DE | 1 079 607 | 4/1960 |
| DE | 1 100 006 | 2/1961 |
| DE | 1 132 901 | 7/1962 |
| DE | 1 161 430 | 1/1964 |
| EP | 784056 A1 | 7/1997 |
| WO | WO 8505047 | 11/1985 |

OTHER PUBLICATIONS

CA:112:38601 abs of Kecheng Xiangjiao Gongye by Nan, C. 12(5) pp. 293-296 1989.*
Stantke, P., & Schmitz, J., Influence of Tin—Addition To A Copper Catalyst On Direct Synthesis, Silicon for the Chemical Industry (2000), pp. 227-233, Trodheim, Norway.
Stantke, P., New Copper Oxide Base Catalyst for the Rochow Synthesis with Low BET (1998), 227-238, Trodheim, Norway.
Bonitz, E., Reactions of Elementary Silicon, Angew. Chem. internal. Edit. (1966), pp. 462-469, vol. 5, No. 5, Germany.
Zapletal, V., Jedlicka, J. & Ruzicka, V., Die Thermische Zerselzung Einiger Metallformate, Collection Czechoslov. Chem. Commun. (1957), pp. 171-174, vol. 22, Czechoslovakia.
Donaldson, J.D., & Knifton, J.F., Tin (II) Formate, J. Chem. Soc. (1964), pp. 4801-4803, U.K.

* cited by examiner

*Primary Examiner*—Shailendra Kumar

(57) ABSTRACT

A Direct Synthesis of making organohalosilanes with greater selectivity to the dialkyldihalosilane is disclosed herein. By using nanosized copper catalyst precursors, and preferably nanosized promoters as well, D/T values of greater than 10, and preferably greater than 15, are obtainable with silicon conversions in excess of 80 wt. %. Shorter induction times are realized using the nanosized copper catalysts in the Direct Synthesis. The nanosized copper catalyst precursors most preferably have an average particle size of less than 100 nanometers.

44 Claims, No Drawings

ROCHOW-MÜLLER DIRECT SYNTHESIS USING NANOSIZED COPPER CATALYST PRECURSORS

This application claims priority from U.S. Provisional Patent Application Ser. No. 60/250,915 filed on Dec. 1, 2000, which is herein incorporated by reference in its entirety.

BACKGROUND OF THE INVENTION

1. Field of the Invention

This invention is directed to the Direct Synthesis of organohalosilanes, and in particular, to the Direct Synthesis of organohalosilanes wherein a higher selectivity for the dialkyldihalosilanes is achieved.

2. Description of Related Art

The Rochow-Muller Direct Synthesis is the one-step preparation of organohalosilanes from copper-activated silicon and an organohalide. This reaction was disclosed in U.S. Pat. No. 2,380,995 to Rochow which issued Aug. 7, 1945, and in German Patent No. DE5348. The Direct Synthesis produces a mixture of silicon-containing products of the following general formulae: $RSiX_3$, $R_2SiX_2$, $R_3SiX$, $R_4Si$, $SiX_4$, $HSiX_3$, $RSiHX_2$, $R_2SiHX$, and $R_nSi_2X_{6-n}$, wherein R is a hydrocarbon, X is a halogen, and n is an integer less than or equal to 6.

Organosilanes such as methylchlorosilanes and phenylchlorosilanes are typically synthesized in fluidized bed reactors via the Direct Synthesis. Controlling and improving process performance to favor the formation of the dihalo moiety, $R_2SiX_2$, over the trihalo moiety, $RSiX_3$, is an ongoing objective of researchers and manufacturers. The preference for the diorganodihalosilane is referred to as its selectivity. The selectivity is defined as the gravimetric ratio $R_2SiX_2/RSiX_3$, abbreviated as D/T. Higher values are desirable. Oftentimes the selectivity is reported as the inverse ratio T/D, thus, a lower value would be desirable. Among the factors known to influence selectivity are choice of copper catalyst; identity, concentration, and ratio of promoters; composition of the silicon; reaction conditions; fluidization rate; and organohalide conversion.

Generally, fluidized bed reactors are used in commercial practice of the Direct Synthesis because they afford a good balance of gas-solid mass transfer at short contact times, good heat removal, high selectivity to dimethyldichlorosilane, and silicon conversions of about 80 to 95 wt. %. Yet, there is a need for more efficient heat removal and improved performance from Direct Synthesis reactors. Poor heat removal manifests itself as "hot spots" on which methyl chloride cracking occurs. Cracking ultimately leads to undesirable by-products such as methyltrichlorosilane, methyldichlorosilane, and trichlorosilane which diminish the formation and selectivity to dimethyldichlorosilane. Thus, more efficient heat removal and/or elimination of hot spots would improve selectivity to the desired dihalo product, $R_2SiX_2$.

Slurry reactors for the Direct Synthesis of organohalosilanes can provide better results than the prior art fluidized bed reactors. In a slurry reactor, catalytically activated silicon particles are suspended in a thermally stable, high boiling heat transfer medium wherein the reaction with the organohalide occurs at an elevated temperature. This type of reactor is taught in U.S. Pat. No. 3,505,379 to Bonitz et al. which issued on Apr. 7, 1970, U.S. Pat. No. 3,641,077 to Rochow which issued on Feb. 8, 1972, U.S. Pat. No. 3,775,457 to Muraoka et al. which issued on Nov. 27, 1973, and U.S. Pat. No. 5,728, 858 to Lewis et al. which issued on Mar. 17, 1998, and assigned to the assignee of the present invention.

German Patent No. DE887343 teaches that silicon and copper powders may be dispersed in liquid paraffin and reacted with methyl chloride to yield methylchlorosilanes. Copper usage was 10 wt. % based on a weight of silicon charged into the reactor.

German Patent Application No. DE 1100006, and German Patent Nos. DE1161430 and DE1132901 teach the preparation of chlorosilanes, methylchlorosilanes and ethylchlorosilanes from the reaction of the corresponding alkyl halide with so-called "active silicon" and ferrosilicon in a liquid paraffin slurry at 180° C. to 200° C. The "active silicon" was made by the action of chlorine on calcium disilicide. No copper was used in some of the experiments. Other solvents used include silicone oils, high boiling polychlorosilanes, and alkylsilicates. The results are summarized in Bonitz, E., *Angewandte Chemie. International Edition*, Vol. 5, No. 5, pp. 462–469 (1966).

German Patent No. DE1079607 discloses a process for slurry-phase activation of silicon and silicon alloys with copper. However, the copper source, such as copper (II) acetylacetonate, must be soluble in the reaction solvent. Solvents used include paraffins, silicate esters, and alkylchloropolysilanes.

German Patent No. DE920187 prefers the use of molten salts as solvents in slurry reactors for the Direct Synthesis of organohalosilanes.

In the fluidized bed Direct Synthesis of organohalosilanes, copper and copper salts, chlorides, and oxides, are used as catalysts to activate the silicon. Typically, the copper catalysts have particle sizes of about 1 to 10 microns and are considerably smaller than those of the silicon particles. Solid promoters of similar particle size are used in the Direct Synthesis to enhance selectivity to the dialkyldihalosilane. Therefore, fluidization velocity is important so that the largest silicon particles are suspended in the organohalide gas stream. However, this fluidization velocity oftentimes exceeds the escape velocity of the smallest copper catalyst and promoter particles from the reactor bed. As a result, the copper catalyst and promoters are rapidly elutriated from the reactor and their consumption is increased, thereby increasing operational costs.

Bearing in mind the problems and deficiencies of the prior art, it is therefore an object of the present invention to provide a method of making organohalosilanes using the Direct Synthesis with greater selectivity to the dialkyldihalosilane.

It is another object of the present invention to provide a method of making organohalosilanes using the Direct Synthesis with more efficient heat removal and/or elimination of hot spots.

A further object of the invention is to provide a method of making organohalosilanes using the Direct Synthesis with lower amounts of catalyst and promoters.

It is yet another object of the present invention to provide a composition useful in the method of making organohalosilanes using the Direct Synthesis.

Still other objects and advantages of the invention will in part be obvious and will in part be apparent from the specification.

SUMMARY OF THE INVENTION

The above and other objects and advantages, which will be apparent to one of skill in the art, are achieved in the present invention which is directed to, in a first aspect, a method for Direct Synthesis of organohalosilanes comprising the steps of:

providing silicon;
providing an organohalide of formula RX wherein R is a saturated or unsaturated aliphatic or aromatic hydrocarbon radical having from 1 to 10 carbon atoms, and X is a halogen;
providing a copper catalyst precursor selected from the group consisting of copper metal, copper (I) oxide, copper (II) oxide, copper (I) chloride, copper (II) chloride, copper (I) carboxylates, copper (II) carboxylates, other copper salts, and mixtures thereof, the copper catalyst precursor having an average particle size from about 0.1 to about 600 nanometers;
reacting the silicon, the organohalide and the copper catalyst precursor for a time and temperature to effectuate high selectivity to diorganodihalosilanes.

Preferably, a thermally stable solvent is provided. The solvent is preferably selected from the group consisting of linear and branched paraffins, cycloparaffins, naphthalenes, alkylated benzenes, dialkylated benzenes, aromatic ethers, and polyaromatic hydrocarbons, the solvents having a boiling point above 250° C. It is advantageous to have a gravimetric ratio of solids to solvent of about 1:1 to about 1:4.

Preferably, the step of providing one or more promoters comprises providing one or more promoters selected from the group consisting of zinc, cadmium, antimony, phosphorus, arsenic, lanthanides, alkali metal halides, tin, and related compounds, the promoters having an average particle size of less than 1000 nanometers. The promoters may be provided in amounts of about 0.005 to about 0.50 wt. % zinc, about 0.0005 to about 0.01 wt. % tin, about 0.001 to about 0.20 wt. % phosphorus, and about 0.0005 to about 0.05 wt. % antimony based on an amount of the silicon.

Preferably, the present method is performed in a slurry reactor in which the silicon, the organohalide, the copper metal catalyst, and the one or more promoters are slurried in the reactor with a thermally stable solvent.

Preferably, the step of providing an organohalide of formula RX comprises providing an organohalide of formula RX wherein R is methyl, ethyl, vinyl, allyl, or phenyl. Some preferred organohalides include methyl chloride, methyl bromide, ethyl chloride, vinyl chloride, and chlorobenzene.

Preferably, the step of providing a copper catalyst precursor comprises providing a copper catalyst precursor having a surface area greater than about 5 $m^2/g$ and an average particle size from about 0.1 to about 500 nanometers, more preferably, a copper catalyst precursor having a surface area greater than about 10 $m^2/g$ and an average particle size from about 0.1 to about 100 nanometers. Preferably, the copper catalyst precursor has a lead concentration of less than about 0.005 wt. % based on an amount of the copper catalyst precursor and less than 0.001 wt. % lead based on an amount of the silicon. It is also possible, and may be desirable, to provide a copper catalyst precursor generated in situ during the Direct Synthesis. Preferably, the step of providing a copper catalyst precursor comprises providing a copper catalyst precursor in an amount from about 0.08 to about 1 parts by weight catalyst per 100 parts by weight silicon In another aspect, the present invention provides a method of synthesizing organohalosilanes having high selectivity to dialkyldihalosilanes comprising the steps of:

providing a slurry reactor having an agitation means therein and a thermally stable reaction solvent;
providing silicon having a particle size of no greater than 500 microns with a concentration of lead of less than 0.0001 wt. % based on a weight of the silicon;
providing a copper catalyst precursor comprising copper, one or more copper salts, or a mixture thereof having an average particle size from about 0.1 to about 600 nanometers;
activating the silicon with the copper catalyst precursor to form copper-silicon intermetallics;
providing one or more promoters selected from the group consisting of zinc, cadmium, antimony, phosphorus, arsenic, lanthanides, alkali metal halides, tin, and related compounds having an average particle size of less than 1000 nanometers; and
providing an organohalide to react with the copper activated silicon and thereby selectively forming a dialkyldihalosilane.

Preferably, the step of providing a copper catalyst precursor comprises providing a copper catalyst precursor selected from the group consisting of copper, copper (I) oxide, copper (II) oxide, copper (I) chloride, copper (II) chloride, copper (I) carboxylates, copper (II) carboxylates, and mixtures thereof. The step of activating the silicon with the copper catalyst precursor to form copper-silicon intermetallics may comprise activating the silicon in situ. The step of activating the silicon with the copper catalyst precursor to form copper-silicon intermetallics preferably comprises activating the silicon with the copper catalyst precursor and promoters in a dry state in a separate rotary, vibrating, fluidized bed reactor or fixed bed reactor. Preferably, the step of activating the silicon with the copper catalyst precursor occurs in the presence of a gaseous hydrogen halide or an alkylhalosilane. Foam control agents may be added to the slurry reactor. The Direct Synthesis may be conducted in a continuous or batch fashion.

In yet another aspect, the present invention is directed to a method of controlling a Direct Synthesis for making an organohalosilane comprising the steps of:

providing silicon;
providing one or more copper catalyst precursors having an average particle size of less than 600 nanometers;
providing one or more promoters selected from the group consisting of zinc, cadmium, antimony, phosphorus, arsenic, lanthanides, alkali metal halides, tin, related compounds, and mixtures thereof having an average particle size of less than 500 nanometers, wherein a Zn/Sn gravimetric ratio is about 12 to about 60, and a Zn/Cu gravimetric ratio is about 0.04 to about 0.2;
heating the silicon, the one or more copper catalyst precursors, and the one or more promoters;
forming copper-silicon intermetallics for reaction with an organohalide; and
maintaining the zinc to tin ratio during the Direct Synthesis wherein selectivity for a dialkyldihalosilane is greater than 10 D/T.

Preferably, the heating step occurs at a temperature greater than 180° C. in the presence of hydrogen chloride such that a short induction time is required prior to reaction with an organohalide. The step of providing one or more copper catalyst precursors may comprise providing one or more copper catalyst precursors selected from the group consisting of copper, copper (I) oxide, copper (II) oxide, copper (I) chloride, copper (II) chloride, copper (I) carboxylates, copper (II) carboxylates, and mixtures thereof. Preferably, the step of heating the silicon, the one or more copper catalyst precursors, and the one or more promoters occurs as a slurry in a thermally stable solvent at a temperature of about 150 to about 350° C. for about 0.01 to about 24 hours.

In still yet another aspect, the present invention is directed to a composition useful for the Direct Synthesis of organohalosilanes comprising:

silicon having a particle size of less than about 500 microns;

one or more copper catalyst precursors having an average particle size from about 0.1 to about 600 nanometers, a surface area as low as 0.1 m$^2$/g, in an amount from about 0.01 to about 5 parts by weight per 100 parts of the silicon such that about 0.008 to about 4.5 parts elemental copper is present based on 100 parts by weight of the silicon;

one or more promoters present in an amount of about 0.05 to about 0.50 wt. % zinc, about 0.0005 to about 0.015 wt. % tin, about 0.001 to about 0.20 wt. % phosphorus, and about 0.0005 to about 0.05 wt. % antimony based on an amount of the silicon, having an average particle size of less than 1000 nanometers; and a thermally stable reaction solvent present in an amount that provides a gravimetric ratio of solids to solvent of about 1:2 to about 1:4.

Preferably, the copper catalyst precursors are selected from the group consisting of copper metal, copper (I) oxide, copper (II) oxide, copper (I) chloride, copper (II) chloride, copper (I) carboxylates, copper (II) carboxylates, other copper salts, and mixtures thereof. Preferably, the copper catalyst precursor is present in an amount of about 0.05 to about 2 parts by weight per 100 parts of the silicon, more preferably, in an amount of about 0.08 to about 1 parts by weight per 100 parts of the silicon. For optimal performance, the Zn/Sn gravimetric ratio is about 12 to 60.

DESCRIPTION OF THE PREFERRED EMBODIMENT(S)

The present invention unexpectedly provides a method of making organohalosilanes using the Direct Synthesis that has a greater selectivity to the dialkyldihalosilane while utilizing smaller amounts of catalysts and promoters. More specifically, the method of the present invention teaches a variation of the Direct Synthesis wherein the silicon has been activated with nanosized copper and/or copper salts and reacted with an organohalide in the presence of nanosized promoters. Greater selectivity and smaller amounts of catalyst and promoters used in the Direct Synthesis result in tremendous cost savings to silane manufacturers.

The Direct Synthesis produces silicon-containing products of the formulae: $RSiX_3$, $R_2SiX_2$, $R_3SiX$, $R_4Si$, $SiX_4$, $HSiX_3$, $RSiHX_2$, $R_2SiHX$, and $R_nSi_2X_{6-n}$ wherein R is a hydrocarbon and X is a halogen. The desired product is $R_2SiX_2$, also referred to as the dialkyldihalosilane product. Preferably, R is a saturated or unsaturated aliphatic or aromatic hydrocarbon radical and X is a halogen atom. A more preferable reaction product is where R is methyl or phenyl, and X is chlorine or bromine. Advantageously, the present invention provides enhanced reaction conditions with high selectivity for making dimethyldichlorosilane and diphenyldichlorosilane. Utilizing the present invention, D/T values of greater than 10, and preferably greater than 15, are obtainable. Silicon conversions in excess of 80 wt. %, and preferably in excess of 90 wt. %, are realized with the present invention.

Preferably, the method of the present invention utilizes a slurry reactor although other reactors may also be contemplated.

Rate is reported either as the temporal consumption of silicon or organohalide, or as the temporal formation of organosilanes. Typical units are wt. % silicon conversion per hour, or kilograms of organohalosilanes per kilogram of silicon per hour. Stability is the maintenance of desirable rate and selectivity until all raw materials are consumed, or consumed beyond a preset silicon conversion.

Nanosized Copper Catalyst Precursors

The copper catalysts employed in the present invention are in actuality catalyst precursors. When the reaction mixture comprising a slurry of nanosized copper and/or copper salts, silicon, promoters, and solvent, is heated, the copper and/or copper salts interact with the silicon to produce the actual catalytic phases that react with the organohalide.

The nanosized copper catalyst precursors used in the present invention comprise copper, copper (I) oxide, copper (II) oxide, copper (I) chloride, copper (II) chloride, copper (I) carboxylates, copper (II) carboxylates, other copper salts, and mixtures thereof. The copper catalyst precursors preferably have an average particle size of about 0.1 to about 600 nanometers. More preferably, the copper catalyst precursors have an average particle size of about 0.1 nanometers to about 500 nanometers. And most preferably, copper catalyst precursors have an average particle size of about 0.1 to about 100 nanometers. The BET surface area of the precursors may be as low as about 0.1 m$^2$/g, preferably greater than about 10 m$^2$/g, and most preferably, greater than 15 m$^2$/g.

The nanosized copper catalyst precursors used in the present invention are present in an amount effective to catalyze the Direct Synthesis reaction. An effective amount ranges from about 0.01 to about 5 parts by weight nanosized copper catalyst precursor per 100 parts by weight silicon. Preferably, the amount of copper catalyst precursor is about 0.05 to about 2 parts by weight nanosized copper catalyst precursor per 100 parts by weight silicon. An especially preferred amount is about 0.08 to about 1 parts by weight nanosized copper catalyst precursor per 100 parts by weight silicon. Expressed in terms of parts by weight elemental copper per 100 parts by weight silicon, the preferred range is about 0.008 to about 4.5 parts copper, more preferably about 0.03 to about 1.8 parts copper, and most preferably, 0.05 to about 0.9 parts copper.

It is preferable that the nanosized copper catalyst precursors used in the present invention are anhydrous. However, material containing adventitious water or water of hydration may also be utilized. If a hydrated nanosized copper catalyst precursor is contemplated, provisions should be made in the reaction apparatus so that the organohalosilane reaction product does not come in contact with the water formed during dehydration and thermal decomposition of the copper catalyst precursor. Furthermore, it is preferable to delay addition of the organohalide into the reaction mixture until the dehydration and thermal decomposition are complete.

Trace impurities and extraneous matter might be present in the nanosized copper catalyst precursors depending upon the method and conditions of its preparation. Trace amounts of aluminum, barium, calcium, lead, phosphorus, tin and zinc may be present. The lead concentration of the copper catalyst precursor is preferably less than 50 parts per million. Polymers, surfactants, and boron contamination might be present in nanosized copper generated by borohydride reduction in the presence of stabilizing polymers, or in reverse micelles and microemulsions.

Synthesis of these superfine copper catalyst precursors by physical and chemical methods are known in the art. Nanosized material produced from these known methods is usable in the instant invention provided it does not impair the selectivity, rate, and/or stability of the Direct Synthesis of the organohalosilanes. Physical methods of preparing the nanosized copper catalyst precursors include laser ablation, evaporation, sputtering, and ion bombardment, amongst others. When a physical method is used to prepare the nanosized copper catalyst precursor, it is desirable, but not essential, that the particles be collected in the reaction solvent or on the silicon to be reacted as they are generated. For example, laser ablation of powdered copper compounds like cuprous chloride (CuCl) and cuprous oxide may be performed in the reaction solvents. Additionally, nanometer sized clusters of copper and copper compounds generated by evaporation, sputtering or ion bombardment may be collected on the silicon. Copper silicon intermetallics and solid solutions may thereby be formed. The clusters may also be quenched in the reaction solvents used in the present invention. If additives such as surfactants and polymers are used for stabilization against sintering and agglomeration, they must not impair the selectivity, rate and stability of the organohalosilane Direct Synthesis. Some silicones, organofluoro surfactants, and fluorosilicone surfactants useful as foam control agents might also be used for dispersing the nanoparticulates generated.

It is preferred that the nanosized copper and copper oxides used in the present invention are prepared by the methods taught in U.S. Pat. No. 4,539,041 to Figlarz et al., which issued on Sep. 3, 1985, U.S. Pat. No. 5,759,230 to Chow et al., which issued on Jun. 2, 1998, and, most preferably, by the method taught in co-pending patent application entitled PREPARATION OF NANOSIZED COPPER AND COPPER COMPOUNDS, Attorney Docket No. 0066-OS, filed on even date herewith. The copper catalyst precursors prepared by these methods are most preferred for the Direct Synthesis of methylchlorosilanes and phenylchlorosilanes.

Promoters

Promoters are used in the Direct Synthesis of organohalosilanes to enhance reaction rates and afford greater selectivity to the desired organohalosilane. Promoters shown to be effective in promoting diorganodihalosilane formation utilizing gas-solid reactors (e.g., fixed bed, stirred bed, and fluidized bed reactors) include zinc, cadmium, antimony, phosphorus, arsenic, lanthanides, alkali metal halides, and tin. Brasses, zinc chloride, zinc oxide, zinc formate, and zinc carbonate are also known to be effective promoters.

In practicing the instant invention, reduced quantities of promoters are used in comparison to prior art methods. Thus, it is possible to achieve good performance in the lower end of prior art concentration ranges or outside prior art concentration ranges discouraged by the teachings of the art. It is preferable to use slurry phase reactors in practicing the present invention, thus, using low promoter concentrations do not pose a problem as it does in fluidized bed or stirred bed reactors where fine particle elutriation and evaporation of volatile metal compounds occur. Both solid and liquid forms of the promoters may be used and are particularly effective in the slurry phase process of the instant invention. When using a slurry phase reactor, the promoters are added to the reaction slurry at the onset and periodically, or continuously, thereafter.

Accordingly, an effective amount of zinc as a promoter is about 0.05 to about 0.5 wt. % (or about 500 to about 5000 parts per million (ppm)) based on an amount of silicon charged to the reactor. Preferably, the concentration of zinc is about 0.09 to about 0.5 wt. %. Effective zinc promoters include, but are not limited to, elemental zinc, zinc oxide, zinc chloride, zinc carbonate, zinc formate, dimethyl zinc chloride and methyl zinc chloride.

On the same basis, the tin concentration may be about 0.0005 to about 0.015 wt. % (or about 5 to about 150 ppm), and more preferably, about 0.001 to about 0.008 wt. %. Effective tin promoters include, but are not limited to, metallic tin, stannous oxide, stannic oxide, stannous chloride, stannic chloride, copper stannate, stannous formate, methylchlorostannanes, copper-tin alloys, and lead-free bronzes and brasses.

Phosphorus concentration may be present at about 0.001 to about 0.2 wt. % (or about 10 to about 2000 ppm), and preferably, at about 0.002 to about 0.15 wt. % based on an amount of silicon charged to the reactor. Phosphorus promoters include, but are not limited to, elemental phosphorus; metal phosphides of calcium, copper, aluminum, and zinc; phosphorus trichloride; trimethylphosphine; and trimethylphosphite.

Antimony ranges from about 0.0005 to about 0.05 wt. % (or about 5 to about 500 ppm), and preferably about 0.001 to about 0.04 wt. %. Antimony may be added as the metal, oxides, chlorides or acetates.

In order to provide exceptional performance in the Direct Synthesis in accordance to the present invention, it is advantageous to have the zinc to tin gravimetric ratio (Zn/Sn) from about 12 to about 60, more preferably, about 30 to 55. An optimum zinc to copper gravimetric ratio (Zn/Cu) is found to be about 0.04 to about 0.2, more preferably about 0.075 to about 0.175. Less indicative of desirable performance is the tin to copper gravimetric ratio (Sn/Cu).

Nanoparticulate forms of promoters, having an average particle size of less than 1000 nanometers, preferably less than 500 nanometers, are particularly effective in practicing the instant invention. Nanosized promoters may be generated in situ by thermal decomposition. For example, thermal decomposition of zinc formate in alkylated benzene solvents produces zinc oxide particles of about 10 to about 90 nanometers. This particular zinc oxide is very effective as a promoter in the instant invention.

Liquid forms of promoters also work well wherein liquid refers to the physical state of the promoter at normal room temperature of 15 to 30° C. at 1 atmosphere. Exogenously prepared nanosized zinc, zinc oxide, tin, tin oxide and other promoters may be introduced into the reaction slurry as dispersions in hydrocarbons such as hexane, toluene or the reaction solvent. Under the high temperature conditions of the Direct Synthesis, these dispersions of promoters are volatilized to provide wide dispersion of the promoter over the copper activated silicon particles. Dimethyl zinc chloride, methyl zinc chloride, methylchlorostannanes, phosphorus trichloride, and trimethylphosphine are examples of effective liquid promoters and may be used as a hydrocarbon solutions. These promoter solutions and dispersions provides a simple and precise way of adding the promoters into the organohalide feed stream or directly into the reaction slurry. Thus, maintenance of promoter concentrations and ratios within optimum ranges lead to desirable reaction performance of the Direct Synthesis.

Silicon

The silicon used in the method of the present invention may be any commercially available silicon in particulate form. It may be produced by any of the known methods in the art such as casting, water granulation, atomization, and acid leaching. Special types of chemical grade silicon containing certain levels of the promoters within the ranges discussed above may also be suitable provided that copper is not one of the alloying elements. A typical, commercial grade silicon may consist essentially of about 98.5 wt. % silicon, about 0.1 to about 0.7 wt. % iron, about 0.05 to about 0.7 wt. % aluminum, about 0.001 to about 0.3 wt. % calcium, less than 0.001 wt. % lead, and less than 0.1 wt. % water based on a total weight of the silicon.

When using a slurry reactor, smaller particle sizes are preferred for ease of dispersion in the slurry, faster reaction, and minimization of erosion in the reactor. The silicon particles should be no larger than 500 microns. A particle size distribution wherein at least 90 wt. % of the silicon is between about 1 to about 300 microns is preferred. More preferred is a particle size distribution wherein at least 90 wt. % of the silicon is between about 1 to about 100 microns. The smaller particle size range includes the dust remaining from silicon grinding which is normally discarded as waste or used in non-chemical applications. Also, silicon having a particle size distribution wherein at least 90 wt. % of the silicon particles is less than 1,000 nanometers is also suitable for use.

Unexpectedly, the present invention using nanosized copper catalyst precursors provides marked improvement in the reactivity of silicon produced by acid leaching. Traditionally, silicon produced by acid leaching, e.g., SILGRAIN® from Elkem ASA of Oslo, Norway, does not afford good yields of organosilanes when activated by conventional methods. However, with the nanosized copper catalyst precursors, rate, selectivity and stability are improved.

Organohalide

The organohalide used in the method of the present invention for reaction with the copper activated silicon has the general formula RX. R is a saturated or unsaturated aliphatic or aromatic hydrocarbon radical. Examples of R are methyl, ethyl, vinyl, allyl and phenyl. X is a halogen atom, preferably chlorine or bromine. Suitable organohalides include, but are not limited to, methyl chloride, methyl bromide, ethyl chloride, vinyl chloride, and chlorobenzene. Preferred are methyl chloride and chlorobenzene.

It is desirable but not necessary to remove trace contaminants or prevent the introduction of volatile inhibitors, e.g., $CO$, $CO_2$, $O_2$, $SO_2$, $H_2O$, $CH_3OH$, of the Direct Synthesis of organohalosilanes. For large scale processes, it is advisable to purify the methyl chloride to remove nitrogen and hydrocarbon contaminants such as methane and isobutane which may have formed during the Direct Synthesis prior to recycle back into the reactor. Although the nitrogen and hydrocarbon contaminants are not poisonous to the formation of the desired organohalosilane, their presence does decrease the partial pressure of the organohalide available for reaction.

Standard commercial grade methyl chloride with a minimum purity of 99.6% is acceptable as a raw material in the Direct Synthesis of dimethyldichlorosilane. Chlorobenzene, preferably, should have a purity of greater than or equal to 99% when used in the Direct Synthesis of diphenyldichlorosilane. It is best to vaporize the chlorobenzene prior to its injection into the reaction slurry. With any organohalide used, it must not contain any impurities which may impair the rate, selectivity or stability of the Direct Synthesis.

Reaction Solvent

Solvents for the Direct Synthesis performed in accordance with the present invention, and preferably using a slurry reactor, maintain the copper activated silicon and other reaction solids in a well dispersed state and facilitate mass transfer of the organohalide to catalytic sites. The preferred solvents useful in practicing the present invention are thermally stable compounds or mixtures that do not degrade under the high temperatures during activation and reaction conditions. Structurally, the solvents are linear or branched paraffins, cycloparaffins, alkylated benzenes, dialkylated benzenes, aromatic ethers, and polyaromatic hydrocarbons. The polyaromatic hydrocarbons may have aromatic rings which are fused together as in naphthalene, phenanthrene, anthracene, and fluorene derivatives. The aromatic rings may be joined together by single carbon-carbon bonds as in biphenyl and terphenyl derivatives, or they may be joined by bridging alkyl groups as in diphenylethanes and tetraphenylbutanes.

One class of preferred solvents is the high temperature stable organic solvents typically used as heat exchange media. Examples include THERMINOL® 59, THERMINOL® 60, and THERMINOL® 66 from Solutia, Inc., St. Louis, Mo.; DOWTHERM® HT from Dow Chemical Co., Midland, Mich.; MARLOTHERM® S, and MARLOTHERM® L from Condea Chemie GmbH, Marl, Germany; and polyphenyl ethers having normal boiling points above 250° C. THERMINOL® 59 is a mixture of alkyl-substituted aromatic compounds recommended for use between −45 to 315° C. THERMINOL® 60 is a mixture of polyaromatic compounds with an average molecular weight of about 250. Its optimum temperature range is from −45 to 315° C. as well. THERMINOL® 66 and DOWTHERM® HT are mixtures of hydrogenated terphenyls with an average molecular weight of about 240 and a maximum temperature limit of about 370° C. MARLOTHERM® S is a mixture of isomeric dibenzylbenzenes, and MARLOTHERM® L is a mixture of isomeric benzyl toluenes. Both may be used at temperatures up to about 350° C. Especially preferred are THERMINOL® 59, THERMINOL® 66, DOWTHERM® HT, MARLOTHERM® S, and MARLOTHERM® L.

Suitable alkylated benzenes for the practice of the instant Direct Process are dodecylbenzene, tridecylbenzene, tetradecylbenzene and their mixtures such as are sold by Vista Chemical Company under the trade name NALKYLENE®, and by Condea Augusta s.p.a. under the trade names ISORCHEM® and SIRENE®. NALKYLENE® 550BL, NALKYLENE® 550L, NALKYLENE® 500, NALKYLENE® 501, NALKYLENE® 600L, NALKYLENE® V-7050, and NALKYLENE® V-3060 L-B are preferred reaction solvents for use with the nanosized CuCl, nanosized copper and nanosized copper oxide precursors. NALKYLENE® V-3060 L-B is a linear dialkylbenzene product having a boiling point greater than 400° C. NALKYLENE® V-7050 is comprised of dialkylated benzenes with initial boiling point greater than 320° C. It is a particularly preferred reaction solvent for the present invention.

Cycloparaffins or naphthenes are components of white mineral oils, petroleum distillates and some fuels. White mineral oils and petroleum distillates also contain normal and branched paraffins. Suitable examples of commercial products containing paraffins, and useful as reaction solvents for this invention are the white mineral oils, CARNATION® 70, KAYDOL®, LP-100 and LP-350, and the petroleum distillates, PD-23, PD-25 and PD-28, all of which are sold by Crompton Corporation under the WITCO® trade mark. Other examples of naphthenes useful as reaction solvents are decahydronaphthalene, perhydroanthracene, perhydrophenanthrene, perhydrofluorene and their alkylated derivatives, perhydroterphenyl, perhydrobinaphthyl and their alkylated derivatives. Direct Syntheses with the paraffin solvents are desirably conducted at temperatures less than 300° C. It is additionally desirable that all solvents be free of components with normal boiling points less than 200° C.

Mixtures of alkylated benzenes, cycloparaffins, normal and branched paraffins, and polyaromatic hydrocarbons are also useful as reaction solvents for the instant invention.

Used solvents may be treated for removal of solids, metal salts, disilanes and other accumulated impurities, prior to recycle and reuse in the slurry reactor. Remediation comprises filtration of solids and stripping of the filtrate at temperatures up to about 250° C. (atmospheric pressure) to remove lower boiling hydrocarbons, disilanes and siloxanes.

Silicon, nanosized copper catalyst precursor, promoter and solvent may be added together in the reactor in any order. The solvent is present in an amount sufficient to disperse the solid and gaseous reactants homogeneously. Generally, reactions are initiated with gravimetric ratio of solids to solvent between 1:2 and 1:4, preferably 1:1 to 1:4. However, as the silicon is consumed during batchwise Direct Synthesis, the solvent to solids ratio will increase. The ratio may be maintained within narrow limits of the preferred range for continuous reactions.

Activation Conditions

Activation is the process of incorporating catalyst, and if desired, other auxiliary agents, into the silicon to make it reactive with the organohalide. Activation may be performed in the same reactor used for the Direct Reaction of the organohalide, or in a separate reactor. In the latter case, the activated silicon is typically and desirably transported to the synthesis reactor in an anhydrous, non-oxidizing atmosphere. Transportation of the activated silicon as a slurry in the reaction solvent is especially preferred.

Activation of nanosized copper catalyst precursors and silicon in a slurry reactor is performed between about 20 to about 400° C., preferably between about 150 to about 350° C., with mixtures containing about 0.01 to about 50 wt. % copper relative to silicon. In one embodiment, the agitated slurry is heated to about 200 to about 300° C. in an inert gas (for example, nitrogen or argon) atmosphere for about 0.01 to about 24 hours prior to the injection of the organohalide. In an alternate embodiment, gaseous hydrogen halide (for example, HCl), or methylchlorosilane (for example, $CH_3SiCl_3$ and/or $(CH_3)_2SiCl_2$) vapor is used in place of the inert gas. In yet another embodiment, hydrogen, carbon monoxide or another reducing gas may be used to activate the slurry. Whatever the method employed, the time and temperature must be sufficient to bring about effective copper-silicon activation and avoid long induction periods, significant loss of diorganodihalosilane selectivity, and/or formation of hydrocarbons and water during the Direct Synthesis. It is not necessary that all of the silicon be present during the activation step. For example, a portion of the silicon to be used and all of the nanosized copper catalyst precursor may be activated in the reaction solvent and the remaining silicon added thereafter.

In a most preferred embodiment of the instant invention, hydrogen chloride, HCl, activation occurs in a slurry. Gaseous HCl is introduced into the slurry comprising solvent, silicon, nanosized copper catalyst precursor and, optionally, promoters. Zinc and tin promoters, especially the nanosized ones, are preferably present in the slurry during the HCl activation step. The temperature of the activation may be about 20 to about 400° C., preferably about 150 to about 350° C. Activation temperature and time are selected to effect minimum conversion of silicon by HCl, short induction periods, high selectivity to the diorganodihalosilane and fast reaction rates.

All of the silicon, nanosized copper catalyst precursor and promoters may be activated in situ by introducing the organohalide vapor, optionally admixed with inert gas, into the agitated slurry during heating, or after the desired reaction temperature has been attained. Reaction ensues beyond some minimum temperature, typically greater than about 180° C. at atmospheric pressure.

Activation may also be performed with the silicon, nanosized copper catalyst precursors and promoters in their dried state in rotary, vibrating, fluidized bed or fixed bed reactors. Thereafter, the activated silicon is transported to the slurry reactor for reaction with the organohalide.

Activation of mixtures containing silicon and nanosized copper catalyst precursors may produce hydrocarbons, HCl, trichlorosilane, silicon tetrachloride and other compounds, depending on the specific precursor charged and the activation method used. These compounds are preferably volatilized and absent prior to the start of the Direct Synthesis of the organohalosilanes. If they are present in the synthesis reactor or in the product retention vessel, they oftentimes contribute to gel formation, poor reaction selectivity and reduced diorganodihalosilane recovery. When nanosized CuCl, or another halogen-containing nanosized copper precursor or HCl, is used, provision must be made to protect the reactor and ancillary equipment from corrosion.

Reaction Conditions

Reactors may be operated in a batchwise or continuous mode. In batchwise operation, a single addition of silicon and copper catalyst is made to the reactor at the outset and organohalide is added continuously, or intermittently, until the silicon is fully reacted, or reacted to a desired degree of conversion. In continuous operation, copper-activated silicon and promoters are added to the reactor initially and thereafter to maintain the solids content and composition of the slurry within desired limits.

In its preferred form in accordance with the present invention, the Direct Synthesis of diorganodihalosilanes is conducted in a continuously agitated slurry reactor containing solvent, silicon, nanosized copper catalyst precursor, promoters and foam control agents in contact with gaseous organohalide. The reactor may have a single nozzle or multiple nozzles for the introduction of gas. A means of continuous or intermittent addition of nanosized copper catalyst precursor-silicon mixture, or of silicon, and of promoters is also provided. Means for continuous removal and recovery of the volatile reaction products and unreacted organohalide are also desirably provided. Separation and purification of the diorganodihalosilane products are optimally performed by continuous fractional distillation.

When the initial loading of silicon and nanosized copper catalyst precursor is activated according to the methods of the instant invention, continuous slurry phase Direct Synthesis of diorganodihalosilanes is advantageously continued by adding silicon and promoters, or silicon and promoters containing less nanosized copper catalyst precursor than that initially added. In this way, the copper concentration of the slurry is controlled to minimize the transformation of the organohalide to hydrocarbons and hydrogen halides. Formation of the latter ultimately results in formation of organotrihalosilanes and organohalohydrosilanes and in reduced selectivity to the diorganodihalosilanes.

The brevity of the induction period of the Direct Synthesis in accordance with the present invention is dependent upon the rate of silicon conversion. Steady-state performance is attained prior to the conversion of about 10 wt. % of the silicon originally charged to the reactor. In most cases, steady-state is achieved at less than 10 wt. % silicon conversion, and preferably between 1 and 7 wt. % silicon conversion. With such low rates of silicon conversion, the induction times are considerably shorter to achieve an earlier steady state in the reaction.

The reaction is generally conducted at temperatures above about 180° C., yet below such a temperature as would degrade or decompose the reactants, solvents or desired products. Preferably, the reaction temperature is maintained in a range from about 250 to about 450° C. The reaction of methyl chloride with the copper-activated silicon of the present invention is preferably operated at about 250 to about 350° C., whereas the reaction of chlorobenzene is preferably operated at about 300 to about 450° C. The pressure at which the reaction is conducted may be varied from subatmospheric to superatmospheric. Atmospheric pressure and pressures up to about 5 atmospheres are generally employed.

Preferably, the contents of the reaction mixture are agitated to maintain a well-mixed slurry of the copper-activated silicon particles and gaseous organohalide in the solvent. Agitation speed and power must be sufficient to keep the largest particles suspended in the solvent, and not settle on the bottom of the reactor. It must also afford optimum gas-liquid-solid mass transfer.

The exit line carrying the reaction mixture from the reactor is preferably well insulated to insure that the organohalosilanes remain gaseous. Solvent vapors and droplets present in the gas stream may be removed by cooling to temperatures that are still above the boiling points of the organohalosilanes, and/or by passing the reaction mixture through a de-mister. Volatile metal salts such as $AlCl_3$, $FeCl_2$, $SnCl_2$, $TiCl_4$, $ZnCl_2$ and mixed metal salts (for example, $CuAlCl_4$) may also be removed thereby.

The presence of gaseous alcohol, hydrogen gas and other gases in the reactor may occasionally lead to foaming. This is undesirable since it may result in loss of solvent and copper-activated silicon from the reactor. The addition of foam control agents, preferably silicon-containing foam control agents such as SAG® 1000, SAG® 100, SAG® 47, available from OSi Specialties/Crompton Corporation, Greenwich, Conn., and FS 1265 from Dow Corning, Midland, Mich., will negate or control this problem. SAG® 1000, SAG® 100, SAG® 47 are compositions comprising polydimethylsilicones and silica. FS 1265 contains fluorinated silicones, for example, poly(dimethylsiloxane-co-trifluoropropylmethylsiloxanes). The foam control agent must be durable such that a single addition at the outset of a batch reaction is sufficient to avoid or mitigate foam formation until all of the silicon has been consumed.

At constant temperature, the reaction rate depends critically on the surface area and particle size of the silicon, the concentrations of nanosized copper and promoters, and on the feed rate of the organohalide. Higher rates are obtained at higher surface areas, finer particle sizes, balanced copper and promoter concentrations and higher organohalide feed rates. These parameters are selected so that a safe, economically sustainable product output is realized without endangerment to people, property and the environment.

High selectivity to diorganodihalosilanes, high reaction rates and stable performance are realized when nanosized copper catalyst precursors and nanosized or liquid promoters are used in the present invention. All of these advantages of the instant invention will be illustrated herein below by example.

Performance Advantages

In accordance with the present invention, substantial advantages are achieved in the Direct Synthesis of dimethyldichlorosilanes and diphenyldichlorosilanes by use of the nanosized copper catalyst precursors, particularly nanoparticulate copper (I) oxide, for silicon activation. The induction period is shortened. In comparison with a fluidized bed reactor, less copper is used to effect the reaction on account of the increased dispersion of copper on silicon. Reaction rates are faster and overall activity is so enhanced that silicon samples that are inactive or ineffective with conventional copper catalyst precursors may be made reactive and productive. Compared to a fluidized bed reactor, less promoters are required to achieve stable rates, high selectivity, and high silicon conversion. Raw material wastage and operational costs are reduced. Additionally, since the nanosized copper catalyst precursor may be prepared in a vessel separate from the reactor used for the Direct Synthesis, water generation from the thermal decomposition of $Cu(OH)_2$ is eliminated as a source of operational problems. Continuous Direct Synthesis of organohalosilanes is thereby facilitated.

EXAMPLES

The following Examples illustrate the preferred embodiments of the instant invention. They are not intended to limit the scope of the invention. Rather, they are presented to facilitate experimental verification of the invention by those of ordinary skill in the art.

TABLE I

Abbreviations and Units Used

| ABBREVIATION | MEANING | ABBREVIATION | MEANING |
|---|---|---|---|
| g | Gram | D | $(CH_3)_2SiCl_2$ |
| kg | Kilogram | T | $CH_3SiCl_3$ |
| cm | Centimeter | M | $(CH_3)_3SiCl$ |
| $m^2/g$ | Square meters per gram | MD | $CH_3SiHCl_2$ |
| h | Hour | TC | $HSiCl_3$ |
| nm | Nanometer | % Si/h | Weight percent silicon converted per hour |
| μ | Micron | cSt | Centistokes |
| wt. % | Weight percent | ppm | Parts per million |

Equipment Used for Illustrative Examples

A 2.0 L glass reactor was used for all of the experiments presented in the illustrative Examples. Agitation was provided by two pitched, glass blades attached to an axial shaft. The bottom blade was 5.7 cm in diameter and the top blade 3.9 cm. The blades were separated by 3.8 cm. A Model BDC 1850 Stirrer manufactured by Caframo Limited, Ontario, Canada, with digital speed control was the power source for agitation. An electric heating mantle controlled by a digital heater/temperature was used to heat the reactor.

Methyl chloride was supplied to the reactor from a cylinder via a calibrated flowmeter. The gas was preheated to 100° C. by transit through a 30 cm long×0.32 cm diameter coiled, stainless steel tube placed in a silicone oil bath. Stainless steel tubing from the oil bath to the reactor inlet was also controlled at 100° C. with electrical heating tape.

Chlorobenzene can be supplied to the reactor from a 1 L reservoir via a calibrated FMI pump. The oil bath (described above) and transfer lines can be controlled at 160° C. to keep the chlorobenzene (normal boiling point 137° C.) gaseous.

Reaction products and unreacted organohalide exited the reactor through a 40 cm long×2.5 cm diameter Vigreux column controlled at 100° C. This served as an entrainment separator for solvent droplets and metal salts. The gaseous reaction mixture was then admitted to a condenser, cooled to about 0° C. with chilled silicone oil, before it was collected in a sampling flask attached to a dry ice-isopropanol cold finger. Gas leaving the collection flask was cooled in a second dry ice-isopropanol cold finger before being vented to the hood through a vapor lock bubbler. The bubbler contained silicone oil and had an extra opening for the release of over-pressure.

Samples were collected in flat-bottomed flasks and set aside for evaporation of unreacted methyl chloride prior to gas chromatographic analysis. The evaporation step was not necessary with chlorobenzene reactions.

Gas chromatographic analysis of the reaction product was performed on a Hewlett Packard 5890E chromatograph. The column was 305 cm×0.635 cm (inner diameter) packed with 30 wt. % OV-210 on acid washed Chrom P. Programs, flow rates and other conditions were appropriate for the samples analyzed as would be known by one of skill in the art.

Materials Used for Illustrative Examples

Chemical grade silicon from Pechiney Electrometallurgie of Paris, France, was used in the experiments of the illustrative Examples. About 72 wt. % of the silicon particles were between 45 to 300 microns. Chemical analysis revealed 0.35 wt. % iron, 0.05 wt. % calcium, 0.21 wt. % aluminum, 0.02 wt. % titanium, 4 ppm copper, less than about 3 ppm zinc, 20 ppm phosphorus, less than about 10 ppm tin, 0.30 wt. % oxygen.

Nanosized copper (I) oxide was prepared by thermal decomposition of KOCIDE® $Cu(OH)_2$ in NALKYLENE® 500 as taught in co-pending patent application entitled PREPARATION OF NANOSIZED COPPER AND COPPER COMPOUNDS, Attorney Docket No. 0066-OS. The resultant particles were about 20 to about 100 nanometers in size.

Zinc formate was synthesized as described in Zapletal, V. et al., *Collection of Czech. Chem. Comm.*, 22 (1957) pp. 171–174, and tin formate as in Donaldson, J. D. et al., *J. Chemical Society* (1964) pp. 4801–4803. Thermal decomposition of these formates was studied by thermal gravimetric analysis in flowing nitrogen. Solid residues from thermal decomposition of the salts in NALKYLENE® 500 solvent were analyzed by x-ray powder diffraction (XRD) and high resolution scanning electron microscopy (HRSEM). Zinc formate produced hexagonally shaped crystals of zinc oxide, ZnO, with dimensions of about 10 to about 90 nanometers. The photomicrograph showed that tin formate had decomposed to micron-sized slabs of stannous oxide, SnO, from which nanometer size fragments had become separated. FS1265 is a commercial brand of fluorosiloxanes available in a range of viscosities from Dow Corning.

Examples 1 to 9

These Examples illustrate that selectivity (D/T) greater than about 10 can be obtained at copper concentrations 0.5 to 5 wt. % by controlling the zinc and tin concentrations and the Zn/Sn gravimetric ratio.

In each experiment, KOCIDE® $Cu(OH)_2$ (~58 wt. % Cu) was first decomposed to nanosized $Cu_2O$ by heating it in NALKYLENE® 500. The quantities of Cu(OH)2 used are shown in Table II below. The hydroxide was mixed with 250 g NALKYLENE® 500 in a four neck round bottom flask. The flask was fitted with a mechanical stirrer, temperature-controlled heating mantle, air-cooled condenser and nitrogen sparge tube. The mixture was heated to 250° C. This temperature was maintained for 1 hour. Thereafter, the mixture was cooled and allowed to settle overnight. NALKYLENE® 500 was decanted away from the dark brown, solid residue, which was later transferred to the slurry reactor for the Direct Synthesis.

The Direct Synthesis slurry reactor was charged with 1.0 kg NALKYLENE® V-7050, 0.5 kg silicon, 2.2 g FS 1265 having a viscosity of 300 cSt, 2.2 g FS 1265 having a viscosity of 1000 cSt, and the nanosized $Cu_2O$. $Sn(OOCH)_2$ (56.75 wt. % Sn) and $Zn(HCOO)_2 \cdot 2H_2O$ (34.31 wt. % Zn) were charged in the amounts shown in Table II. The contents of the reactor were then agitated at 820 rpm and heated to 300° C. Both metal formates decomposed to their respective nanosized oxides in the hot hydrocarbon solvent. Nitrogen was introduced into the reactor at a rate of 0.4 L/min $N_2$ during the heating and subsequent reaction with methyl chloride. With the temperature at 300° C., 6.5 g $CH_3SiCl_3$ was pumped through the vaporizer, with the assistance of flowing nitrogen, into the reactor within a 2 minute period. A nitrogen purge was maintained for 1 hour before methyl chloride was injected. The $CH_3SiCl_3$ was condensed and collected separately from the reaction product.

The methyl chloride flow was 0.8 L/min. The reaction was continued for a total of 24 to 30 hours before termination. No further additions of $Zn(OOCH)_2 \cdot 2H_2O$ and $Sn(OOCH)_2$ were made to the reactor during the experiments. Weighed samples were collected at 30 to 60 minute intervals and analyzed by gas chromatography after most of the unreacted methyl chloride had evaporated. Selectivity (D/T) and the silicon conversion at which steady-state was attained were calculated from the data.

TABLE II

Amounts of Copper Catalyst Precursors and Promoters in Examples 1 to 9

| EX | $Cu(OH)_2$ (g) | $Zn(HCOO)_2$ (g) | $Sn(HCOO)_2$ (g) | Cu (wt. %) | Zn (ppm) | Sn (ppm) |
|---|---|---|---|---|---|---|
| 1 | 7.503 | 1.39 | 0.025 | 0.87 | 953.8 | 28.38 |
| 2 | 7.503 | 2.207 | 0.025 | 0.87 | 1514.4 | 28.38 |
| 3 | 7.503 | 2.207 | 0.05 | 0.87 | 1514.4 | 56.75 |
| 4 | 7.503 | 7.357 | 0.025 | 0.87 | 5048.4 | 28.38 |
| 5 | 7.503 | 7.357 | 0.05 | 0.87 | 5048.4 | 56.75 |
| 6 | 15.006 | 2.207 | 0.025 | 1.74 | 1514.4 | 28.38 |
| 7 | 15.006 | 2.207 | 0.05 | 1.74 | 1514.4 | 56.75 |
| 8 | 15.006 | 7.357 | 0.025 | 1.74 | 5048.4 | 28.38 |
| 9 | 15.006 | 7.357 | 0.05 | 1.74 | 5048.4 | 56.75 |
| 10 | 30.012 | 2.207 | 0.1 | 3.48 | 1514.4 | 113.5 |
| 11 | 30.012 | 2.207 | 0.05 | 3.48 | 1514.4 | 56.75 |

In Table III, the data show that (D/T) values greater than 10 were observed at copper levels in the range of 0.5 to 4 wt. % (relative to the amount of silicon charged). These desirable (D/T) values occurred at particular promoter concentrations and ratios. The optimum zinc concentration was 900 to 5500 ppm and the tin concentration was 20 to 120 ppm. Optimum zinc to tin gravimetric ratios (Zn/Sn) spanned 12 to 60. Optimum zinc to copper gravimetric ratios (Zn/Cu) were 0.04 to 0.2. Tin to copper gravimetric ratios did not appear to be indicative of desirable performance. Typically, the onset of steady-state at desirable D/T values occurred at silicon conversions less than 10 wt. % and, in most cases, at silicon conversions less than 7 wt. %.

TABLE III

Selectivity in Relation to Promoter/Copper Ratios in Examples 1 to 9

| EXAMPLE | Zn/Sn | Zn/Cu | Sn/Cu | D/T | % Si Conv. at Onset of Steady-State |
|---|---|---|---|---|---|
| 1 | 33.61 | 0.109 | 0.00326 | 15.19 | 4.70 |
| 2 | 53.37 | 0.174 | 0.00326 | 20.14 | 6.66 |
| 3 | 26.69 | 0.174 | 0.00652 | 20.29 | 6.24 |
| 4 | 177.92 | 0.580 | 0.00326 | 2.89 | 9.48 |
| 5 | 88.96 | 0.580 | 0.00652 | 2.72 | 5.44 |
| 6 | 53.37 | 0.087 | 0.00163 | 20.16 | 3.66 |
| 7 | 26.69 | 0.087 | 0.00326 | 21.43 | 1.62 |
| 8 | 177.92 | 0.290 | 0.00163 | 6.51 | 2.28 |
| 9 | 88.96 | 0.290 | 0.00326 | 9.35 | 4.41 |
| 10 | 13.34 | 0.043 | 0.00326 | 10.47 | 2.88 |
| 11 | 26.69 | 0.043 | 0.00163 | 12.52 | 2.34 |

Example 10

This Example illustrates the slurry phase Direct Synthesis of methylchlorosilanes from silicon activated with nanosized copper (I) oxide and nanosized promoters ZnO and SnO, both of which were generated in situ in the reactor.

To 7.503 g KOCIDE® Cu(OH)$_2$ having about 58 wt. % Cu, was added 2.207 g Zn(OOCH)$_2$.2H$_2$O (34.31 wt. % Zn), mixed and stirred in 250 g NALKYLENE® 500 in a four neck round bottom flask. The flask was fitted with a mechanical stirrer, temperature-controlled heating mantle, air-cooled condenser and nitrogen sparge tube. The mixture was heated to 250° C. This temperature was maintained for 1 hour. Thereafter, the mixture was cooled and allowed to settle overnight. NALKYLENE® 500 was decanted away from the dark brown, solid residue, which was later transferred to the slurry reactor for the Direct Synthesis.

The Direct Synthesis slurry reactor was charged with 0.7 kg NALKYLENE® V-7050, 0.5 kg silicon, 2.2 g FS 1265 (300 cSt), 2.2 g FS 1265 (1000 cSt), and 0.035 g Sn(OOCH)$_2$. The mixture of nanosized Cu$_2$O and ZnO was slurried in additional NALKYLENE® V-7050 and transferred to the reactor. A total of 301.6 g solvent was used in three aliquots to effect complete transfer. The contents of the reactor were then agitated at 820 rpm and heated to 300° C. Nitrogen was introduced at a rate of 0.4 L/min during the heating and subsequent reaction with methyl chloride. With the temperature at 300° C., 11.5 g CH$_3$SiCl$_3$ was pumped through the vaporizer, with the assistance of flowing nitrogen, into the reactor within a 2 minute period. A nitrogen purge was maintained for 1 hour before methyl chloride was injected. The CH$_3$SiCl$_3$ was condensed and collected separately from the reaction product.

Methyl chloride flow rate was 0.8 L/min. The reaction was continued for a total of 24 hours before termination. Samples were collected hourly and analyzed by gas chromatography after most of the unreacted methyl chloride had evaporated. During the experiment, periodic additions of Zn(OOCH)$_2$ and Sn(OOCH)2 were made to the reactor to maintain D/T and silicon conversion rate at desirable levels. Both metal formates decomposed to their respective nanosized oxides in the hot hydrocarbon solvent. Earlier experiments had shown that addition of Sn(OOCH)$_2$ equivalent to about 10 to about 40 ppm tin increased the Direct Synthesis rate considerably. However, if the zinc concentration was insufficient, the synthesis produced mostly TC, MD and T, and only negligible amounts of D. Thus, 4 to 5 g Zn(OOCH)$_2$ was added every 3 to 5 hours and 0.011 to 0.025 g Sn(OOCH)$_2$ was added every 10 to 12 hours.

After an induction period of about 2 hours, during which D/T was 8 to 11, D/T values increased to 16 to 25 for the remaining 22 hours of the experiment. 75.6 wt. % of the silicon charged was converted to methylchlorosilanes in 24 hours of reaction. Thus, the average rate was 3.15 wt. % Si/h. Average crude product composition at steady-state is shown in Table II below. (CH$_3$)$_2$SiCl$_2$ accounted for 90 wt. % of the product. Average D/T selectivity was 23.61.

TABLE IV

Average Crude Product Composition of Example 10 at Steady State

| COMPONENT | WEIGHT PERCENT |
|---|---|
| CH$_3$Cl | 18.16 |
| CH$_3$SiHCl$_2$ | 0.55 |
| (CH$_3$)$_3$SiCl | 1.48 |
| CH$_3$SiCl$_3$ | 3.12 |
| (CH$_3$)$_2$SiCl$_2$ | 73.67 |
| (CH$_3$)$_n$Si$_2$Cl$_{6-n}$ (n = 2,3,4) | 3.02 |

GC/MS was performed on selected samples to identify the silane compounds in the product. In addition, to the principal compounds listed above, the following trace and minor products were also present: CH$_3$SiCl$_2$F, C$_2$H$_5$(CH$_3$)$_2$SiCl, [CH$_3$SiHO]$_4$, [CH$_3$SiHO]$_5$, [(CH$_3$)$_2$SiO]$_4$, [CH$_3$SiHO]$_4$ [(CH$_3$)$_2$SiO], Cl$_2$CH$_3$SiSiCl$_2$CH$_3$, Cl$_2$CH$_3$SiSiCl(CH$_3$)$_2$. Paraffinic and olefinic hydrocarbons and alkylated benzenes were also detected.

The data show that the selective, fast and stable, slurry-phase Direct Synthesis of methylchlorosilanes was accomplished with the use of nanosized Cu$_2$O as the catalyst precursor and nanosized ZnO and SnO as the promoters. Based on the silicon charged to the reactor, the initial copper concentration was 0.87 wt. %, the initial zinc concentration was 1845 ppm and the initial tin concentration was 39 ppm.

Examples 11 to 14

The experiments were conducted as described above for Examples 1 to 10. Examples 11 and 12 were duplicate experiments using the copper, zinc and tin concentrations disclosed in Example 1 above. Data for raw material quantities used in Examples 13 and 14 are shown in Table V.

TABLE V

Amounts Of Copper Catalyst Precursors and Promoters Used In Examples 11 to 14

| EXAMPLE | Cu(OH)$_2$ (g) | Zn(HCOO)$_2$ (g) | Sn(HCOO)$_2$ (g) | Cu (wt. %) | Zn (ppm) | Sn (ppm) |
|---|---|---|---|---|---|---|
| 11 | 7.503 | 1.39 | 0.025 | 0.87 | 953.8 | 28.38 |
| 12 | 7.503 | 1.39 | 0.025 | 0.87 | 953.8 | 28.38 |
| 13 | 7.503 | 2.207 | 0.025 | 0.87 | 1514.4 | 28.38 |
| 14 | 7.503 | 2.983 | 0.025 | 0.87 | 2046.9 | 28.38 |

When the slurry phase Direct Synthesis of this invention is conducted under optimum catalyst and promoter concentrations, it has generally been observed that the content of methylchlorodisilanes is typically less than 5 wt. % of the reaction product at steady-state. Moreover, the cleavable disilanes, $Cl_2CH_3SiSiCl_2CH_3$ and $Cl_2CH_3SiSiCl(CH_3)_2$, account for more than 90 wt. % of the disilane fraction. The advantages of these examples are illustrated in Table VI.

TABLE VI

Silane Product Distribution of Examples 11 to 14 at Steady-State

| EXAM-PLE | MD (wt. %) | M (wt. %.) | T (wt. %) | D (wt. %) | HVS (wt. %) | CDISIL (wt. %) |
|---|---|---|---|---|---|---|
| 11 | 0.65 | 1.50 | 5.28 | 90.29 | 2.28 | 2.28 |
| 12* | 1.15 | 1.87 | 5.73 | 89.39 | 1.24 | 1.24 |
| 13 | 0.94 | 2.56 | 5.34 | 89.15 | 2.01 | 2.01 |
| 14 | 0.83 | 2.95 | 6.64 | 85.27 | 4.31 | 4.31 |

*Product also contained 0.62 wt. % $HSiCl_3$

Table VI also shows the steady-state methylchlorosilane composition of samples from each of Examples 11 to 14. Selectivity (D/T) was 17.09 in Example 11, 15.60 in Example 12, 16.69 in Example 13, and 12.84 in Example 14. Total disilane content (HVS) was less than 5 wt. %. Cleavable disilanes (CDISIL) accounted for all of the disilane fraction.

Example 15

This Example illustrates the slurry phase Direct Synthesis of phenylchlorosilanes using nanosized copper (I) oxide as the copper precursor and nanosized zinc oxide and tin oxide as promoters.

Nanosized copper (I) oxide was prepared by thermal decomposition of 15.006 g KOCIDE® Cu(OH)$_2$ (~58 wt. % Cu) in 250 g NALKYLENE® 500 at 250° C. for 1 hour, as described in Example 1. Following decantation of the hydrocarbon, the nanosized $Cu_2O$ was transferred to the slurry reactor and combined therein with 2.207 g zinc formate, 0.025 g tin formate, 500 g silicon, 1 kg NALKYLENE® V-3060 L-B, 1.8 g FS1265 (1000 cSt) and 2.2 g FS1265 (300 cSt). Nitrogen was introduced at 0.4 L/min. The reaction mixture was stirred at 820 rpm and heated to 400° C. At 300 to 350° C., HCl gas at 0.4 L/min was injected for 15 minutes. $HSiCl_3$, $SiCl_4$ and other volatile products formed were condensed and drained from collection flask. Nitrogen flow was maintained. When the temperature reached 400° C., chlorobenzene at 55.5 g/hour was pumped to the evaporator (160° C.) and vaporized prior to entry into the reactor. Chlorobenzene flow was continued for 8 hours.

The accumulated reaction mixture was analyzed by gas chromatography and found to contain chlorobenzene, phenyltrichlorosilane, and diphenyldichlorosilane.

The present invention achieves the objects recited above. By using nanosized copper catalyst precursors in the Direct Synthesis of organohalosilanes, there are shorter induction times, and greater selectivity in making the desirable dialkyldihalosilane. In using a slurry reactor to run the Direct Synthesis with nanosized copper catalyst precursors, greater dispersion of the copper catalysts is possible thereby eliminating hot spots resulting in more efficient heat removal. The greater dispersion of the nanosized particles allows the use of lower amounts of catalysts and promoters.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A method for Direct Synthesis of organohalosilanes comprising the steps of: providing a slurry of silicon, an organohalide of formula RX wherein R is a saturated or unsaturated aliphatic or aromatic hydrocarbon radical having from 1 to 10 carbon atoms, and X is a halogen, a copper catalyst precursor and one or more promoters in a thermally stable organic liquid solvent, and reacting said silicon, said organohalide and said copper catalyst precursor in said slurry for a time and at a temperature to effectuate high selectivity to diorganodihalosilanes.

2. The method of claim 1 wherein the thermally stable organic liquid solvent has a boiling point above 250° C.

3. The method of claim 1 wherein said thermally stable organic liquid solvent is selected from the group consisting of linear and branched paraffins, cycloparaffins, naphthalenes, alkylated benzenes, dialkylated benzenes, aromatic ethers and polyaromatic hydrocarbons.

4. The method of claim 2 wherein the thermally stable organic liquid solvent is provided in a sufficient amount such that a gravimetric ratio of solids to solvent is about 1:1 to about 1:4.

5. The method of claim 1 wherein the promoters are selected from the group consisting of zinc, cadmium, antimony, phosphorus, arsenic, lanthanides, alkali metal halides and tin.

6. The method of claim 4 wherein the step of providing one or more promoters comprises providing about 0.005 to about 0.50 wt % zinc, about 0.0005 to about 0.01 wt % tin, about 0.001 to about 0.20 wt % phosphorus, and about 0.0005 to about 0.05 wt % antimony based on an amount of said silicon.

7. The method of claim 1 wherein the step of reacting the silicon, organohalide and copper catalyst precursor is performed in a slurry reactor in which said silicon, said organohalide, said copper metal catalyst, and said one or more promoters are slurried in said reactor with the thermally stable organic liquid solvent.

8. The method of claim 1 wherein the silicon has a particle size distribution wherein at least 90 w % of said silicon is between about 1 to about 300 microns.

9. The method of claim 1 wherein the silicon has a particle size distribution wherein at least 90 wt % of said silicon is between about 1 to about 100 microns.

10. The method of claim 1 wherein the silicon has a particle size distribution wherein at least 90 wt % of said silicon is less than 1000 nanometers.

11. The method of claim 1 wherein R is methyl, ethyl, vinyl, allyl, or phenyl.

12. The method of claim 1 wherein organohalide of formula RX is selected from the group consisting of methyl chloride, methyl bromide, ethyl chloride, vinyl chloride, and chlorobenzene.

13. The method of claim 1 wherein the organohalide of formula RX is methyl chloride or chlorobenzene.

14. The method of claim 1 wherein the copper catalyst precursor has a surface area greater than about 5 $m^2$/g and an average particle size from about 0.1 to about 500 nanometers.

15. The method of claim 1 wherein the copper catalyst precursor has a surface area greater than about 10 $m^2$/g and an average particle size from about 0.1 to about 100 nanometers.

16. The method of claim 1 wherein the copper catalyst precursor has a lead concentration of less than about 0.005 wt % based on an amount of said copper catalyst precursor and less than 0.001 wt % based on an amount of said silicon.

17. The method of claim 1 wherein the step of providing a copper catalyst precursor comprises generating the copper catalyst precursor in situ during said direct synthesis.

18. The method of claim 1 wherein the copper catalyst precursor in an amount from about 0.08 to about 1 parts by weight copper catalyst precursor per 100 parts by weight silicon.

19. A method of synthesizing organohalosilanes having high selectivity to dialkyldihalosilanes comprising the steps of: providing a slurry reactor having an agitation means therein and a thermally stable organic liquid reaction solvent; providing silicon having a particle size of no greater than 500 microns with a concentration of lead of less than 0.0001 wt % based on a weight of said silicon; providing a copper catalyst precursor having an average particle size from about 0.1 to about 600 nanometers; activating said silicon with said copper catalyst precursor to form copper activated silicon; providing one or more promoters selected from the group consisting of zinc, cadmium, antimony, phosphorus, arsenic, lanthanides, alkali metal halides and tin, having an average particle size of less than 1000 nanometers; and providing an organohalide to react with the copper activated silicon in a liquid slurry including the thermally stable organic liquid solvent and thereby selectively forming a dialkyldihalosilane.

20. The method of claim 19 wherein the copper catalyst precursor is selected from the group consisting of copper, copper (I) oxide, copper (II) oxide, copper (I) chloride, copper (II) chloride, copper (I) carboxylates, copper (II) carboxylates and mixtures thereof.

21. The method of claim 19 wherein the step of activating said silicon metal with said copper catalyst precursor to form copper activated silicon is performed in situ.

22. The method of claim 19 wherein the step of activating said silicon with said copper catalyst precursor to form copper activated silicon comprises activating said silicon with said copper catalyst precursor and promoters in a dry state in a separate rotary, vibrating, fluidized bed reactor or fix bed reactor.

23. The method of claim 19 wherein said step of activating said silicon with said copper catalyst precursor occurs in the presence of a gaseous hydrogen halide or an alkylhalosilane.

24. The method of claim 19 further including the step of providing foam control agents.

25. The method of claim 19 wherein said method is conducted in a continuous or batch fashion.

26. The method of claim 19 wherein the step of providing said copper catalyst precursor comprises generating the copper catalyst precursors in situ in the reaction solvent.

27. The method of claim 19 further including providing additional silicon, copper catalyst precursors, and promoters.

28. The method of claim 19 further including the recovering, remediating and recycling the thermally stable reaction solvent.

29. A method of controlling a Direct Synthesis for making an organohalosilane comprising the steps of: providing a silicon; providing one or more copper catalyst precursors having an average particle size of less than 600 nanometers; providing one or more promoters selected from the group consisting of zinc, cadmium, antimony, phosphorus, arsenic, lanthanides, alkali metal halides, tin, and mixtures thereof, having an average particle size of less than 500 nanometers; heating said silicon, said one or more copper catalyst precursors, and said one or more promoters in a thermally stable organic liquid solvent; and forming copper activated silicon for reaction with an organohalide in a slurry including the thermally stable organic liquid solvent.

30. The method of claim 29 wherein said heating step occurs at a temperature greater than 180° C. in the presence of hydrogen chloride such that a short induction time is required prior to reaction with an organohalide.

31. The method of claim 29 wherein the one or more copper catalyst precursors are selected from the group consisting of copper, copper (I) oxide, copper (II) oxide, copper (I) chloride, copper (II) chloride, copper (I) carboxylates, copper (II) carboxylates and mixtures thereof.

32. The method of claim 29 wherein the step of heating said silicon, said one or more copper catalyst precursors, and said one or more promoters occurs as a slurry at a temperature of about 150 to about 350° C. for about 0.01 to about 24 hours.

33. A composition useful for the Direct Synthesis of organohalosilanes comprising: silicon having a particle size of less than about 500 microns; one or more copper catalyst precursors having an average particle size from about 0.1 to about 600 nanometers, a surface area as low as 0.1 m$^2$/g, in an amount from about 0.01 to about 5 parts by weight per 100 parts of said silicon; one or more promoters selected from the group consisting of about 0.05 to about 0.50 wt % zinc, about 0.0005 to about 0.015 wt % tin, about 0.001 to about 0.20 wt % phosphorus and about 0.0005 to about 0.05 wt % antimony based on the amount of said silicon, the promoter having an average particle size of less than 1000 nanometers; and a thermally stable organic liquid reaction solvent present in an amount that provides a gravimetric ratio of solids to solvent of about 1:2 to about 1:4.

34. The composition of claim 33 wherein said copper catalyst precursors are selected from the group consisting of copper metal, copper (I) oxide, copper (II) oxide, copper (I) chloride, copper (II) chloride, copper (I) carboxylates, copper (II) carboxylates, other copper salts, and mixtures thereof.

35. The composition of claim 33 wherein said copper catalyst precursor is present in an amount of about 0.05 to about 2 parts by weight per 100 parts of said silicon.

36. The composition of claim 33 wherein said copper catalyst precursor is present in an amount of about 0.08 to about 1 parts by weight per 100 parts of said silicon.

37. The composition of claim 33 the promoters include zinc and tin in amount having a Zn/Sn gravimetric ratio of from about 12 to 60.

38. The method of claim 1 wherein the copper compound is selected from the group consisting of copper, copper (I) oxide, copper (II) oxide, copper (I) chloride, copper (II) chloride, copper (I) carboxylate, copper (II) carboxylate and mixtures thereof.

39. The method of claim 1 wherein the promoters are in liquid form.

40. The method of claim 1 wherein the copper catalyst precursor has an average particle size of less than 600 nanometers, the promoter has an average particle size of less than 1000 nanometers and the silicon has a particle size no larger than 500 microns.

41. The method of claim 1 wherein the copper catalyst precursor has an average particle size of from about 0.1 to about 500 nanometers, the promoter has an average particle size of less than 500 microns and the silicon has a particle size distribution wherein at least 90 wt % of the silicon has a particle size of between about 1 to about 100 microns.

42. The method of claim 1 wherein the copper catalyst precursor has an average particle size of from about 0.1 to about 100 nanometers, and the silicon has a particle size distribution wherein at least 90 wt % of the silicon has a particle size of less than 1000 nanometers.

43. The method of claim 29 wherein the promoters include zinc and tin wherein a Zn/Sn gravimetric ratio is from about 12 to about 60, a Zn/Cu gravimetric ratio is from about 0.04 to about 0.2, and the Zn/Sn gravimetric ratio is maintained during the Direct Synthesis wherein D/T selectivity for a dialkyldihalosilane is greater than 10.

44. The method of claim 33 wherein about 0.008 to about 4.5 parts of elemental copper of the copper catalyst precursor is present based upon 100 parts by weight of silicon.

* * * * *